US005900370A

United States Patent [19]

Running

[11] Patent Number: 5,900,370
[45] Date of Patent: May 4, 1999

[54] PROCESS FOR THE PRODUCTION OF ASCORBIC ACID WITH PROTOTHECA

[75] Inventor: Jeffrey Running, Manitowoc, Wis.

[73] Assignee: Bio-Technical Resources

[21] Appl. No.: 08/485,811

[22] Filed: Jun. 7, 1995

Related U.S. Application Data

[63] Continuation-in-part of application No. 08/196,338, Feb. 10, 1994, abandoned, which is a continuation-in-part of application No. 07/853,476, Mar. 18, 1992, abandoned, which is a continuation-in-part of application No. 07/650,886, Feb. 5, 1991, abandoned, which is a continuation of application No. 06/750,828, Jul. 1, 1985, Pat. No. 5,001,059, and a continuation-in-part of application No. 07/896,724, Jun. 9, 1992, abandoned, which is a continuation of application No. 07/650,886, which is a continuation of application No. 06/750,828, and a continuation-in-part of application No. 07/853,379, which is a continuation-in-part of application No. 07/650,886, which is a continuation of application No. 06/750,828.

[51] Int. Cl.⁶ ..................................................... C12P 7/40
[52] U.S. Cl. ........................ 435/136; 435/137; 435/138; 435/257.1; 435/946; 435/172.1
[58] Field of Search ..................................... 435/136, 137, 435/138, 257.1, 946, 172.1

[56] References Cited

U.S. PATENT DOCUMENTS

| 3,882,635 | 5/1975 | Yamanaka | 47/1.4 |
| 5,001,059 | 3/1991 | Skatrud et al. | 435/137 |

FOREIGN PATENT DOCUMENTS

1522756  8/1978  United Kingdom .

OTHER PUBLICATIONS

Aaronson et al., "The Cell Content and Secretion of Water–Soluble Vitamins by Several Freshwater Algae", *Arch. Microbiol* 112: 57–59, (1977).
Barnett et al., "Quantitative Recovery of Prototheca from the Environment", *Abstracts of the Annual Meeting*, Mm46 p. 143, (1974).
Bayanova and Trubachev, *Prikladnaya Biokhimiya i Microbiologyia* 17: 400–407 (UDC 582. 26: 577.16), (1981).
Becker et al., "Major Results of the Indo–German Algal Project", *Arch Hydrobiol Beih.*, vol. 11, pp. 23–40,(1978).
Casselton et al., "Ammonium Assimilation *Prototheca zopfii* Krüger", *British Phycological Society*, vol. 17, No. 2, pp. 230–231, (1982).
Casselton et al. "Observations on the Nitrogen Metabolism of Prototheca Kr üger", *New Phytol*, vol. 68, pp. 731–749, (1969).
Ciferri, "Spirulina, the Edible Microorganism", *Microbiological Reviews* 47:551–578 (1983).
Considine, "Ascorbic Acid (Vitamin C)" *Van Nostrand's Scientific Encyclopedia*, vol. 1, pp. 237–238, (1989).
Conte, et al., "Taxonomic Implications of Prototheca and Chlorella Cell Wall Polysaccharide Characterization", *Arch. Mikrobiol.*, vol. 92 pp. 227–233, (1973).
Lloyd et al., "The Cell Wall of *Prototheca zopfii*", *J. gen. Microbiol*, 50, pp. 421–427, (Aug. 1967).

Gruen et al., "Determination of Ascorbic Acid in Algae by HPLC on Strong Cation Exchange Resin With Electrochemical Detection", *Analytical Biochemistry* 130: 191–198, (1983).
Huss, et al., Deoxyribonucleic Acid Reassociation in the Taxonomy of the Genus Chlorella, IV. "*Chlorella Protothecoides* and Its Relationship to the Genus Prototheca," *Arch. Microbiol* vol. 150, pp. 509–511 (1988).
Kerfin et al., "Physiological and Biochemical Contributions to the Taxonomy of the Genus Prototheca", *Arch. Microbiol*, vol. 116, pp. 105–107, (1978).
Kessler, "Physiological and Biochemical Contributions to the Taxonomy of the Genus Prototheca, III. Utilization of Organic Carbon and Nitrogen Compounds", *Arch. Microbiol.*, vol. 132, pp. 103–106, (1982).
Kessler, "Physiological and Biochemical Contributions to the Taxonomy of the Genus Chlorella", *Arch. Microbiol*, vol. 113, pp. 139–141, (1977).
Loewus, F.A., "L–Ascorbic Acid: Metabolism, Biosynthesis, Function", *The Biochemistry of Plants*, vol. 3, pp. 77–79 (1980).
Manners, et al., "The Molecular Structures of a Glucan and a Galactan Synthesised by *Prototheca zopfii*", *Carbohydrate Research*, vol. 29, pp. 63–77, (1973).
McNamer et al., "Proline Uptake and Utilization by *Chlorella pyrenoidosa*", *Plant Physiol.* 52: 561–564, (1973).
Nadakavukaren et al., "An Ultrastructural survey of the Genus Prototheca with Special Reference to Plastids", *Mycopathologia*, vol. 61.2, pp. 117–119, (1977).
Padhye, et al., "Rapid Identification of Prototheca Species by the API 20C System", *Journal of Clinical Microbiology*, vol. 10, No. 4, pp. 579–582, (1979).
Pore, "Prototheca Taxonomy", *Mycopathologia*, vol. 90, pp. 129–139, (1985).
Pore, "Taxonomic Status and Experimental Pathology of Prototheca Species", pp. 63–64, (1971).
Pore, "Nutritional Basis for Relating Prototheca and Chlorella," *Canadian Journal of Microbiology*, vol. 18, pp. 1175–1177 (1972).
Pore, et al., "Prototheca Ecology", *Mycopathologia* vol. 81 pp. 49–62, (1983).
Pore, "Selective Medium for the Isolation of Prototheca", *Applied Microbiology*, vol. 26, No. 4, pp. 648–649 (Oct. 1973).
Puel et al., "Etude Ultrastructurale de *Prototheca wickerhamii* (Tubaki et Soneda, 1959) Variations Observees au cours du Cycle Cellulaire", *Annales des Sciences Naturelles*, Seri 13c vol. 4, pp. 15–26, (1982).
Rana et al., "Effects of 2–Deoxy–D–Glucose On The Growth And Metabolism of *Prototheca zopfii* Krüger" *New Phytol.*, vol 73, pp. 663–674, (1974).

(List continued on next page.)

Primary Examiner—Irene Marx
Attorney, Agent, or Firm—Sheridan Ross, P.C.

[57] ABSTRACT

The present invention is directed to methods for the production of ascorbic acid by culturing organisms of the genus Prototheca and recovering ascorbic acid from the fermentation medium.

23 Claims, No Drawings

OTHER PUBLICATIONS

Rehm et al., *Biotechnology*, vol. 1, pp. 247–297, (1981).

Renstrom, et al., "Biosynthesis of L–Ascorbic Acid in *Chlorella pyrenoidosa*", *Plant Science Letters*, vol. 28 pp. 299–305, (1982/83).

Shigeoka et al., "The Effect of Illumination on the L–Ascorbic Acid Content in *Euglena gracilis z*" *Agric. Biol. Chem.* 43: 2053–2058, (1979).

Shigeoka et al., "The Biosynthetic Pathway of L–Ascorbic Acid in *Euglena gracilis z*" *J. Nutr. Sci. Vitaminol* 29: 299–307, (1979).

Subbulakshmi et al., "Effect of Processing on the Nutrient Content of the Green Alga *Scenedesmus acutus*", *Nutrition Reports International*, 14: 581–591, (1976).

Subbulakshmi et al., "Effect of Processing on the Nutrient Content of the Green Alga *Scenedesmus acutus*", *Nutrition Reports International*, 14: 581–591, (1976).

Sudman et al., Studies on the Antigenic Relationships between Prototheca and Chlorella, *Abstracts of the Annual Meeting*, Mm34 p. 141, (1974).

Sudman, et al., "Antigenic Relationships Between Chlorella and Prototheca SPP", *Sabouraudia* vol. 12, pp. 364–370, (1974).

Vaidya et al., "Secretion of a Highly Reducing Substance by Algae in Media and its Probable Role in Crop Physiology", *Science and Culture* 37: 383–384, (1971).

Webster et al., "The Respiratory Chain of Colorless Algae, III. Electron Microsopy", *Ultrastructural Research*, 21, pp. 514–523, (1968).

"Strain Descriptions", *ATCC Culture Catalog, Algae –Protozoa*, p. 51 (1993).

Koenig et al, *System Appl. Microbiol.* vol. 5, pp. 119–123 (1984).

Renstrom et al., *Plant Sci. Lett.*, 28(1982) 299–305.

Aaronson et al., *Algae Biomass*, 1980 Elsevier, pp. 575–601.

Bold et al., "Introduction to the Algae" 1985 pp. 142–143.

PROCESS FOR THE PRODUCTION OF ASCORBIC ACID WITH PROTOTHECA

CROSS-REFERENCE TO RELATED APPLICATIONS

This application is a continuation-in-part of U.S. patent application Ser. No. 08/196,338, filed Feb. 10, 1994, now abandoned which is a continuation-in-part of U.S. patent application Ser. No. 07/853,476, filed Mar. 18, 1992, now abandoned, which is a continuation-in-part of U.S. patent application Ser. No. 07/650,886, filed Feb. 5, 1991, now abandoned, which is a continuation of U.S. patent application Ser. No. 06/750,828, filed Jul. 1, 1985, now U.S. Pat. No. 5,001,059, and a continuation-in-part of U.S. patent application Ser. No. 07/896,724, filed Jun. 9, 1992, now abandoned, which is a continuation of U.S. patent application Ser. No. 07/650,886, filed Feb. 5, 1991, now abandoned, which is a continuation of U.S. patent application Ser. No. 06/750,828, filed Jul. 1, 1985, now U.S. Pat. No. 5,001,059; and a continuation-in-part of U.S. patent application Ser. No. 07/853,379, filed Mar. 18, 1992, now abandoned, which is a continuation-in-part of U.S. patent application 07/650,886, filed Feb. 5, 1991, now abandoned, which is a continuation of U.S. patent application 06/750,828, filed Jul. 1, 1985, now U.S. Pat. No. 5,001,059, the disclosures of which are incorporated herein by reference in their entirety.

FIELD OF THE INVENTION

The present invention relates to the production of ascorbic acid by fermentation of organisms of the genus Prototheca, and the recovery of the ascorbic acid produced for use as a dietary supplement.

BACKGROUND OF THE INVENTION

Nearly all forms of life, both plant and animal, either synthesize ascorbic acid (e.g., Vitamin C) or require it as a nutrient. Ascorbic acid was first identified to be useful as a dietary supplement for humans and animals for the prevention of scurvy. Ascorbic acid, however, also affects human physiological functions such as the adsorption of iron, cold tolerance, the maintenance of the adrenal cortex, wound healing, the synthesis of polysaccharides and collagen, the formation of cartilage, dentine, bone and teeth, the maintenance of capillaries, and is useful as an antioxidant.

For use as a dietary supplement, ascorbic acid can be isolated from natural sources, such as rosehips, synthesized chemically through the oxidation of L-sorbose, or produced by the oxidative fermentation of calcium D-gluconate by *Acetobacter suboxidans*. Considine, "Ascorbic Acid," *Van Nostrand's Scientific Encyclopedia*, Vol. 1, pp. 237–238, (1989). It is also known to obtain predominantly intracellular ascorbic acid through the fermentation of microorganisms of *Chlorella pyrenoidosa*. See U.S. Pat. No. 5,001,059 by Skatrud, which is assigned to the assignee of the present application. While not fully understood, it is believed that ascorbic acid is produced inside the chloroplasts of photosynthetic microorganisms and functions to neutralize energetic electrons produced during photosynthesis. Accordingly, ascorbic acid production is known in photosynthetic organisms as a protective mechanism.

The invention of the present application involves the novel use of microorganisms of the genus Prototheca to produce ascorbic acid. Organisms of the genus Prototheca are not photosynthetic and therefore would not have a need to produce ascorbic acid to function as a protective compound during photosynthesis. Early attempts at classifying organisms of the genus Prototheca identified the organism as a relation to photosynthetic Chlorella on the basis of morphology and life cycle. Modern references which mention such a relationship typically cite references from the early 1900s. For example, Lloyd et al., "The Cell Wall of Prototheca zopfii," *J. Gen. Microbiol.*, 50:421–427 (1968) cites references from 1904, 1913 and 1927.

These early studies, however, were necessarily based on the analytical techniques available at that time. Today, however, Prototheca are not believed to be closely related to ascorbic acid producing species of Chlorella. Many modern references document numerous structural, biochemical and genetic differences between Chlorella and Prototheca.

With regard to structural differences between Prototheca and Chlorella, Webster et al. in "The Respiratory Chain of Colorless Algae, III. Electron Microscopy," *J. Ultrastructure Research*, 21:514–523, (1968), report (1) the presence of multiple Golgi bodies in Prototheca, whereas Chlorella has a maximum of one Golgi body, (2) the presence of vacuoles in Prototheca which are absent in Chlorella, (3) the positioning of mitochondria near the cell walls in Prototheca compared to the positioning of mitochondria in the cup of the chloroplast in Chlorella, (4) the cell wall of Prototheca consists of several layers, whereas the cell wall appears to be one layer in $KMnO_4$-fixed material for Chlorella, (5) the cell wall pulls away from the cytoplasm in $KMnO_4$-fixed material for Chlorella which does not occur for Prototheca, (6) the inward movement of the inner material of the cell wall during division in Prototheca which has not been observed in Chlorella, and (7) the cell wall of Prototheca is more convoluted than that of Chlorella. Accordingly, Webster et al. conclude that the existence of these significant differences in ultrastructure makes the classification of Prototheca as a colorless Chlorella unlikely.

Similarly, Lloyd et al. in "The Cell Wall of *Prototheca zopfii,*" *J. Gen. Microbiol.*, 50:421–427 (1968), report differences in cell wall amino acid constituents of Prototheca and Chlorella, and that Prototheca have nodules on the surface of the cell walls which are absent in Chlorella. Accordingly, Lloyd et al. conclude their findings cast doubt on the relationship of Prototheca as a colorless Chlorella.

With regard to biochemical differences between the genera Prototheca and Chlorella, Casselton et al. in "Observations on the Nitrogen Metabolism of Prototheca Kruger," *New Phytol.*, 68:731–749, (1968), have shown that Prototheca cannot utilize nitrate nitrogen as a nitrogen source, whereas Chlorella can, and further discuss that Prototheca are thiamine dependent, whereas Chlorella are not.

Likewise, Manners et al. in "The Molecular Structures of a Glucan and a Galactan Synthesized by Prototheca zopfii," *Carbohydrate Research*, 29:63–77, (1973), describe significant differences in polysaccharides synthesized by Prototheca and Chlorella. As a result, Manners et al. conclude that the overall results of their investigation would not support the view that Prototheca is simply the colorless counterpart of Chlorella.

With regard to genetic differences between Prototheca and Chlorella, Kerfin et al. in "Physiological and Biochemical Contributions to the Taxonomy of the Genus Prototheca, II. Starch Hydrolysis and Base Composition of DNA," *Arch. Microbiol.*, 116:105–107, (1978), report that the DNA from a strain of Prototheca showed only 3.4% hybridization with labelled DNA from a strain of *Chlorella vulgaris*, which prompted Kerfin et al. to state that this finding indicates that Prototheca is not related to the typical Chlorellas. In addition, Kerfin et al. consider that the guanine and cytosine content of DNA between Chlorella and Prototheca is "quite different".

In summary, prior references which identify Prototheca as an achlorophyllous Chlorella are now viewed with considerable skepticism. Newer analytical techniques have shown such significant structural, biochemical and genetic differences between the two genera that such a relationship is highly unlikely.

SUMMARY OF THE INVENTION

In accordance with the present invention, a process is provided for the production for L-ascorbic acid which includes culturing an organism of the genus Prototheca in a fermentation medium and recovering L-ascorbic acid from the fermentation medium. Organisms of the genus Prototheca which are especially useful in the present invention include, P. zopfii, P. wickerhamii, P. stagnora, P. moriformis and P. ulmea. Preferred for use in the present invention are P. moriformis, P. wickerhamii and P. zopfii. More preferred for use in the present invention are P. moriformis and P. zopfii. In a preferred embodiment of the process, the fermentation medium has a pH of less than about 6. In this manner extracellular ascorbic acid degradation in the fermentation medium is reduced and significant accumulations of ascorbic acid can be attained in the extracellular medium. Extracellular production of ascorbic acid allows for higher productivities and facilitates recovery of the product.

At least a portion of the L-ascorbic acid produced by the cultured organisms is produced extracellularly and is present in the fermentation medium. Typically, at least about 10% of the L-ascorbic acid in the fermentation medium is extracellular, but preferably at least about 25% of the L-ascorbic acid in the fermentation medium is extracellular, and more preferably at least about 50% of the L-ascorbic acid in the fermentation medium is extracellular. Such extracellular L-ascorbic acid can be recovered from the fermentation medium using a recovery process including, but not limited to, ion exchange, chromatography, extraction, solvent extraction, membrane separation, electrodialysis, reverse osmosis, distillation, chemical derivatization and crystallization.

Also in accordance with the present invention, a fermentation culture is provided which includes L-ascorbic acid-producing microalgae in a fermentation medium, wherein the fermentation medium comprises at least about 1 mg/l extracellular L-ascorbic acid and the fermentation medium has a dissolved oxygen content of at least about 20%. Such fermentation media include those having a pH of less than about 6, preferably less than about 5.5 and more preferably less than about 5. Suitable L-ascorbic acid producing microalgae include organisms of the genus Prototheca. Organisms of the genus Prototheca which are especially useful in the fermentation medium include, P. zopfii, P. wickerhamii, P. stagnora, P. moriformis and P. ulmea.

DETAILED DESCRIPTION

The present invention is directed to the production of ascorbic acid by organisms of the genus Prototheca. In particular, the present invention is directed to novel methods for producing L-ascorbic acid by culturing organisms of the genus Prototheca under a variety of culturing conditions.

The production of ascorbic acid by culturing organisms of the genus Prototheca according to the present invention provides significant advantages over known ascorbic acid production methods. One such advantage is that organisms of the genus Prototheca are acidophilic, allowing fermentations to be carried out under low pH conditions, with the fermentation medium pH typically less than about 6. Below this pH, extracellular ascorbic acid produced by Prototheca during fermentation is relatively stable because the rate of oxidation of ascorbic acid in the fermentation medium by oxygen is reduced. Accordingly, high productivity levels can be obtained for producing L-ascorbic acid with Prototheca according to the methods of the present invention. In addition, control of the dissolved oxygen content to very low levels to avoid oxidation of ascorbic acid is unnecessary. Moreover, this advantage allows for the use of continuous recovery methods because extracellular medium can be treated to recover the ascorbic acid product.

Another advantage of the present invention is that the growth and production of organisms of the genus Prototheca has been observed to be tolerant of high levels of ascorbic acid. Desirably, a substantial amount of ascorbic acid can accumulate in the fermentation medium before the production of ascorbic acid by the microorganisms is negatively affected. As a result, ascorbic acid recovery methods are more effective and high productivity levels can be obtained for producing L-ascorbic acid with Prototheca according to the methods of the present invention.

Yet another advantage of the present invention is that substantial quantities of L-ascorbic acid produced by Prototheca organisms is extracellular. As demonstrated below, extracellular concentrations of ascorbic acid are about equal to total ascorbic acid concentrations, thus indicating that intracellular and extracellular concentrations are about equal. As noted above, it is substantially easier to separate extracellular L-ascorbic acid from the fermentation medium than it is to extract intracellular L-ascorbic acid from microorganisms.

A further advantage of the present invention is that the organisms of the genus Prototheca as described and used herein for producing L-ascorbic acid are heterotrophic microorganisms, and can be grown on relatively simple, inexpensive media in order to produce ascorbic acid. In addition, such organisms have been found to have relatively fast growth rates.

PRODUCTION MICROORGANISMS

Microorganisms of the genus Prototheca which are suitable for use in the present invention include those selected from the five known species of Prototheca, namely, P. zopfii, P. wickerhamii, P. stagnora, P. moriformis, and P. ulmea. Preferred for use in the present invention include microorganisms of P. zopfii, P. wickerhamii and P. moriformis. More preferred for use in the present invention include microorganisms of P. zopfii and P. moriformis.

Microorganisms of the genus Prototheca commonly occur in nature and can be readily obtained from various sources, such as, for example, sources described by R. S. Pore in "Prototheca Ecology," *Mycopathologia*, 81:49–62 (1983), which is incorporated herein in its entirety. Organisms of the genus Prototheca have been found in slime flux (i.e., the drainage from tree wounds) of deciduous trees, such as with elm trees (*Ulmus americana*) on the Pennsylvania State University Campus, Pennsylvania. Ibid. Slime flux taken from such trees from metal pipes extending into the heart wood was found to contain $1 \times 10^7$ or more cells of Prototheca sp. per milliliter. Ibid. Organisms of the genus Prototheca have also been found in water and sediments from various streams in West Virginia, such as Deckers Creek, Pompano Run, West Run, Cobun Creek, Scotts Run, Dent's Run, Hartman Run and the Monongahela River. Ibid. Strains of Prototheca have also been isolated from domestic sewage at the Connellsville, Pennsylvania municipal sewage treatment plant; household waste in the Philippines; a sewage lagoon at the 54th USAF base in Thailand,; a street sewage gutter in Port-au-Prince, Haiti; the Unox sewage treatment system in Marietta, Ohio; activated sludge from a chemical digester at Union Carbide in South Charleston, West Virginia; and various sources in France and Spain. Ibid. Yet further, Prototheca have been in some types of foods, such as meats, shellfish and dairy products such as ice cream. Ibid. Thus, Prototheca organisms are ubiquitous and can be collected at these specific locations. Moreover, the large number and wide variety of reported sources indicates that these organisms are widely available throughout the natural environment.

These microorganisms can be detected and isolated from such natural sources through the use of appropriate screening techniques. Such techniques include the use of Prototheca isolation medium (PIM), such as is disclosed by R. S. Pore in "Selective Medium for the Isolation of Prototheca," Appl. Microbiol., 26:648–649 (1973), which is incorporated herein in its entirety. In general, the constituents of PIM include, distilled water, potassium hydrogen phthalate about 10 g/L, sodium hydroxide about 0.9 g/L, magnesium sulfate about 0.1 g/L, potassium hydrogen phosphate about 0.2 g/L, ammonium chloride about 0.3 g/L, glucose about 10 g/L, thiamine hydrochloride about 0.001 g/L, agar about 20 g/L, and 5-fluorocytosine (5-FC) about 0.25 g/L. The medium has a pH in the range of from about 5 to about 5.2. Optionally, hexachlorocyclohexane (about 0.01 g/L before autoclaving) can be added to the PIM for control of arthropod contaminants and fumagillin bicyclohexylamine obtained from Abbott Laboratories in West Chicago, Ill. (about 0.005 g/L dissolved in ethanol and added before autoclaving) can be added to the PIM to control cyst-forming amoebae growth. It will be appreciated that components and amounts of components of PIM can be varied and the medium will still be effective to selectively isolate Prototheca.

The method used for isolating Prototheca on PIM or a variation of PIM depends on the physical characteristics of the sample. Liquid and semisolid specimens, including sediment obtained by centrifugation, are applied directly to the surface of the PIM, or diluted serially and then applied and spread with a sterile glass rod. Solid specimens, however, are chopped and blended in sterile water before plating as previously described. Alternatively, liquid samples or washings of samples such as food are filtered through 3.0 μm or 0.45 μm pore diameter filters. The filters are then pressed particulate side down on PIM and then turned particulate side up on PIM and incubated at a temperature of about 30° C. for a time period of about 48 hours. In general, incubation on PIM at about 30° C. for about 72 hours is adequate for most Prototheca species, however, some strains prefer incubation temperatures of about 25° C. and required incubation for up to about 7 days in order for visible colonies to appear. Colonies of Prototheca can be separated and selected using known techniques, such as smearing the cultures on agar or other suitable medium. Prototheca colonies thus isolated can then be selected and subcultured for use in the present invention as described in more detail below.

In addition to isolating Prototheca from natural sources as described above, various wild type strains are widely available from public depositories for a nominal fee. For example, the American Type Culture Collection (ATCC), located at 12301 Parklawn Drive, Rockville, Md. 20852 lists a number wild type strains of Prototheca as publicly available in their 1993 culture catalog, namely, P. moriformis ATCC 16525, ATCC 16526, ATCC 50081; P. stagnora ATCC 16528; P. ulmea ATCC 50112; P. wickerhamii ATCC 16522, ATCC 16523, ATCC 16529, ATCC 16531, ATCC 30395; and P. zopfii ATCC 16527, ATCC 16532, ATCC 16533, ATCC 3025. In addition, ATCC 75669 is now available. Typically, microorganisms deposited with public depositories such as the American Type Culture Collection are available for as long as the deposited strain is kept alive by the depository. In addition, many depositors make supplemental deposits of a deposited strain which can no longer be kept alive, thereby extending the time periods for which deposited strains are publicly available. A further microorganism that is useful for the production of ascorbic acid according to the present invention is P. moriformis ATCC No. 209681 (NA45-3). ATCC No. 209681, identified as Prototheca moriformis NA45-3, was deposited on Mar. 13, 1998, with the American Type Culture Collection (ATCC), 10801 University Boulevard, Manassas, Va. 20110, USA, under the terms of the Budapest Treaty on the International Recognition of the Deposit of Microorganisms for the Purpose of Patent Procedure.

Prototheca species which have been isolated from nature such as previously described can be differentiated from other Prototheca species according to, for example, their nutritional requirements. For example, in Padhye et al., "Rapid Identification of Prototheca Species by the API 20 C System," J. of Clinical Microbiology, 19:579–582 (1979), which is incorporated herein in its entirety, a method is described for the rapid identification of P. stagnora, P. wickerhamii and P. zopfii species using the API 20C or API 50C clinical yeast identification system, which are commercially available ready-to-use micromethods. According to Padhye et al., such identification can be accomplished within about 3 days, and relies upon the differential assimilation of trehalose and growth of the microorganisms at a temperature of about 37° C. to separate the species.

Microorganisms of the species P. moriformis can be differentiated from P. zopfii on physiological traits. For example, P. moriformis is encapsulated, whereas P. zopfii is not. See, e.g. R. S. Pore, "Prototheca Taxonomy", Mycopathologia, 90:129–139, (1985).

Although five known species of Prototheca are mentioned herein for use in the present invention, it is within the scope of the present invention that, in addition to known species and strains of Prototheca, newly identified species and strains from nature and mutant strains derived from known or newly identified strains can be used to produce ascorbic acid. Moreover, it is recognized that taxonomic classifications of Prototheca organisms has changed and may change in the future. Therefore, the identification of five species of Prototheca is intended to include all known Prototheca despite the fact that other species of Prototheca have been identified in the past. It is believed that the currently accepted taxonomic structure only has the five species identified herein.

Naturally occurring mutants of a parental strain of Prototheca that are capable of producing ascorbic acid can be isolated by, for example, subjecting a parental strain to at least one round of chemical and/or radiation mutagenesis, in order to increase the rate of mutagenesis, thereby increasing the probability of obtaining a microorganism producing increased amounts of ascorbic acid. It will be obvious to one of skill in the art that mutant microorganisms of the present invention also include ascorbic acid-producing microorganisms that can be obtained by genetically engineering microorganisms to produce increased amounts of ascorbic acid. For example, it is within the scope of microorganisms of the present invention to transform microorganisms other than Prototheca with nucleic acid molecules encoding enzymes of the ascorbic acid biosynthetic pathway obtained from Prototheca microorganisms. A Prototheca nucleic acid molecule of the present invention can be obtained from its natural source, either as an entire (i.e., complete) genome or a portion thereof, capable of forming a stable hybrid with the entire gene. A nucleic acid molecule from a strain of Prototheca can also be reproduced using recombinant DNA technology (e.g., polymerase chain reaction (PCR) amplification, cloning) or chemical synthesis. As used herein, a "mutated microorganism" is a mutated parental microorganism in which the nucleotide composition of such microorganism has been modified by mutation(s) that occur naturally, that are the result of exposure to a mutagen, or that are the result of genetic engineering.

FERMENTATION OF PROTOTHECA

According to the method of the present invention, L-ascorbic acid is produced by fermentation of Prototheca. In accordance with the present invention, microorganisms of the genus Prototheca capable of producing L-ascorbic acid are cultured in an effective medium under effective conditions, herein defined as any medium and conditions capable of promoting L-ascorbic acid production. Preferably, the effective medium and conditions also promote rapid algal growth. In particular, the present invention provides a method to produce ascorbic acid, comprising culturing microorganisms of the genus Prototheca in a medium comprising a source of assimilable organic carbon, a source of assimilable nitrogen and appropriate salts and trace metals.

Sources of assimilable carbon which can be used in a suitable fermentation medium include, but are not limited to, sugars and their polymers, including, dextrin, sucrose, maltose, lactose, glucose, fructose, mannose, sorbose, arabinose and xylose; fatty acids; organic acids such as acetate; primary alcohols such as ethanol and n-propanol; and polyalcohols such as glycerine. Preferred carbon sources in the present invention include monosaccharides, disaccharides, and trisaccharides. The most preferred carbon source is glucose.

The concentration of a carbon source, such as glucose, in the fermentation medium should promote cell growth, but not be so high as to repress growth of the microorganism used. Typically, the concentration of a carbon source, such as glucose, in the fermentation medium is greater than about 1 g/L, preferably greater than about 2 g/L, and more preferably greater than about 5 g/L. In addition, the concentration of a carbon source, such as glucose, in the fermentation medium is typically less than about 100 g/L, preferably less than about 50 g/L, and more preferably less than about 20 g/L. It should be noted that references to fermentation component concentrations can refer to both initial and/or ongoing component concentrations.

Sources of assimilable nitrogen which can be used in a suitable fermentation medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of a nitrogen source, such as anhydrous ammonia, in the fermentation medium is greater than about 0.05 g/L, preferably greater than about 0.1 g/L, and more preferably greater than about 0.15 g/L. Beyond certain concentrations, however, the addition of a nitrogen source to the fermentation medium is not advantageous for the growth of the microorganisms. As a result, the concentration of a nitrogen source, such as anhydrous ammonia, in the fermentation medium is less than about 10 g/L, preferably less than about 1 g/L and more preferably less than about 0.25 g/L. Further, in some instances it may be desirable to allow the fermentation medium to become depleted of a nitrogen source during fermentation.

The effective fermentation medium can contain other compounds such as inorganic salts, vitamins, trace metals or growth promoters. Such other compounds can also be present in carbon, nitrogen or mineral sources in the effective medium or can be added specifically to the medium.

The fermentation medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the fermentation medium is greater than about 0.5 g/L, preferably greater than about 1 g/L and more preferably greater than about 2.5 g/L. Beyond certain concentrations, however, the addition of phosphate to the fermentation medium is not advantageous for the growth of the microorganisms. Accordingly, the concentration of phosphate in the fermentation medium is typically less than about 15 g/L, preferably less than about 10 g/L and more preferably less than about 5 g/L.

A suitable fermentation medium can also include a source of magnesium, preferably in the form of a physiologically acceptable salt, such as anhydrous magnesium sulfate, although other magnesium sources in concentrations which contribute similar amounts of magnesium can be used. Typically, the concentration of magnesium in the fermentation medium is greater than about 0.001 g/L, preferably greater than about 0.003 g/L, and more preferably greater than about 0.005 g/L. Beyond certain concentrations, however, the addition of magnesium to the fermentation medium is not advantageous for the growth of the microorganisms. Accordingly, the concentration of magnesium in the fermentation medium is typically less than about 0.1 g/L, preferably less than about 0.05 g/L, and more preferably less than about 0.01 g/L. Further, in some instances it may be desirable to allow the fermentation medium to become depleted of a magnesium source during fermentation.

The fermentation medium can also include a biologically acceptable chelating agent, such as the dihydrate of trisodium citrate. In such instance, the concentration of a chelating agent in the fermentation medium is greater than about 0.2 g/L, preferably greater than about 0.5 g/L, and more preferably greater than about 1 g/L. Beyond certain concentrations, however, the addition of a chelating agent to the fermentation medium is not advantageous for the growth of the microorganisms. Accordingly, the concentration of a chelating agent in the fermentation medium is typically less than about 10 g/L, preferably less than about 5 g/L, and more preferably less than about 2 g/L.

The fermentation medium can also initially include a biologically acceptable mineral acid to neutralize excess nitrogen initially present in the fermentation medium and/or to initially control the pH of the fermentation medium. Biologically acceptable mineral acids include, but are not limited to, sulfuric acid, nitric acid, phosphoric acid and mixtures thereof. In a preferred embodiment of the present invention, the mineral acid used is sulfuric acid. Typically, the initial concentration of the mineral acid, such as 18M sulfuric acid, in the fermentation medium is within the range of from about 0.05 g/L to about 15 g/L, preferably within the range of from about 0.1 g/L to about 5 g/L, and more preferably in the range of from about 0.5 g/L to about 2 g/L.

The fermentation medium can also include iron, however since it is believed iron accelerates the breakdown of extracellular L-ascorbic acid and therefore inhibits L-ascorbic acid accumulation in the medium, the amount of iron present in the fermentation medium is limited. Typically, iron (+2) is present in the fermentation medium during the initial stages of fermentation at a concentration of greater than about 0.1 mg/L, preferably at a concentration greater than about 0.3 mg/L, and more preferably at a concentration greater than about 0.7 mg/L. However, due to the tendency of excess amounts of iron to degrade ascorbic acid in the fermentation medium, iron (+2) is present in the fermentation medium at a concentration of less than about 25 mg/L, preferably at a concentration of less than about 20 mg/L, and more preferably at a concentration of less than about 15 mg/L.

The fermentation medium can also include a biologically acceptable calcium source, including, but not limited to, calcium chloride. Typically, the concentration of the calcium source, such as calcium chloride, dihydrate, in the fermentation medium is within the range of from about 5 mg/L to about 5500 mg/L, preferably within the range of from about 11 mg/L to about 1100 mg/L, and more preferably in the range of from about 55 mg/L to about 220 mg/L.

The fermentation medium can also include a biologically acceptable manganese source, including, but not limited to, manganese sulfate. Typically, the concentration of the manganese source, such as manganese sulfate, monohydrate, in the fermentation medium is within the range of from about 2 mg/L to about 1800 mg/L, preferably within the range of from about 4 mg/L to about 360 mg/L, and more preferably in the range of from about 18 mg/L to about 72 mg/L.

As previously discussed, the fermentation medium can also include trace metals. Such trace metals can be added to the fermentation medium as a solution that, for convenience, can be prepared separately from the rest of the fermentation medium. A suitable trace metals solution for use in the fermentation medium is shown below in Table 1. Typically, the amount of such a trace metals solution in the fermentation medium is greater than about 1 mL/L, preferably greater than about 5 mL/L, and more preferably greater than about 10 mL/L. Beyond certain concentrations, however, the addition of a trace metals to the fermentation medium is not advantageous for the growth of the microorganisms. Accordingly, the amount of such a trace metals solution in the fermentation medium is typically less than about 100 mL/L, preferably less than about 50 mL/L, and more preferably less than about 30 mL/L. It should be noted that, in addition to adding trace metals in a solution, the individual components can be added separately, each within ranges corresponding independently to the amounts of the components dictated by the above ranges of the trace metals solution.

As shown below in Table 1, a suitable trace metals solution for use in the present invention can include cobalt (II) chloride, pentahydrate; boric acid; zinc (II) sulfate, heptahydrate; sodium molybdate, dihydrate; vanadyl sulfate, dihydrate; nickel (II) nitrate, hexahydrate; and sodium selenite.

TABLE 1

TRACE METALS SOLUTION

| COMPOUND | CONCENTRATION OF METAL (mg/L) |
|---|---|
| Cobalt (II) chloride, pentahydrate | 40 |
| Boric acid | 160 |
| Zinc (II) sulfate, heptahydrate | 400 |
| Sodium molybdate, dihydrate | 19 |
| Vanadyl sulfate, dihydrate | 20 |
| Nickel (II) nitrate, hexahydrate | 8 |
| Sodium selenite | 16 |

The microorganisms of the genus Prototheca of the present invention can be cultured in conventional fermentation modes, which include, but are not limited to, batch, fed-batch, and continuous. It is preferred, however, that the fermentation be carried out in fed-batch mode. In such a case, during fermentation some of the components of the medium are depleted. It is possible to initiate fermentation with relatively high concentrations of such components so that growth is supported for a period of time before additions are required. The preferred ranges of these components are maintained throughout the fermentation by making additions as levels are depleted by fermentation. Levels of components in the fermentation medium can be monitored by, for example, sampling the fermentation medium periodically and assaying for concentrations. Alternatively, once a standard fermentation procedure is developed, additions can be made at timed intervals corresponding to known levels at particular times throughout the fermentation. As will be recognized by those in the art, the rate of consumption of nutrient increases during fermentation as the cell density of the medium increases. Moreover, to avoid introduction of foreign microorganisms into the fermentation medium, addition is performed using aseptic addition methods, as are known in the art. In addition, a small amount of anti-foaming agent may be added during the fermentation.

The temperature of the fermentation medium can be any temperature suitable for growth and ascorbic acid production. For example, prior to inoculation of the fermentation medium with an inoculum, the fermentation medium can be brought to and maintained at a temperature in the range of from about 20° C. to about 45° C., preferably to a temperature in the range of from about 25° C. to about 40° C., and more preferably in the range of from about 30° C. to about 38° C.

As noted above, a significant advantage of the present invention is that Prototheca are acidophilic organisms, and thus, the present process can be conducted at low pH. The benefit of this process is that at low pH, extracellular ascorbic acid produced by the organism is degraded at a reduced rate than if the fermentation medium was at higher pH. For example, prior to inoculation of the fermentation medium with an inoculum, the pH of the fermentation medium can be adjusted, and further monitored during fermentation. Typically, the pH of the fermentation medium is brought to and maintained below about 6, preferably below 5.5, and more preferably below about 5. The pH of the fermentation medium can be controlled by the addition of ammonia to the fermentation medium. In such cases when ammonia is used to control pH, it also conveniently serves as a nitrogen source in the fermentation medium.

The fermentation medium can also be maintained to have a dissolved oxygen content during the course of fermentation to maintain cell growth and to maintain cell metabolism for L-ascorbic acid formation. The oxygen concentration of the fermentation medium can be monitored using known methods, such as through the use of an oxygen probe electrode. Oxygen can be added to the fermentation medium using methods known in the art, for example, through agitation and aeration of the medium by stirring or shaking. Preferably, the oxygen concentration in the fermentation medium is in the range of from about 20% to about 100% of the saturation value of oxygen in the medium based upon the solubility of oxygen in the fermentation medium at atmospheric pressure and at a temperature in the range of from about 30° C. to about 40° C. Periodic drops in the oxygen concentration below this range may occur during fermentation, however, without adversely affecting the fermentation.

Although aeration of the medium has been described herein in relation to the use of air, other sources of oxygen can be used. Particularly useful is the use of an aerating gas which contains a volume fraction of oxygen greater than the volume fraction of oxygen in ambient air. In addition, such aerating gases can include other gases which do not negatively affect the fermentation.

In an embodiment of the fermentation process of the present invention, a fermentation medium is prepared as described above. This fermentation medium is inoculated with an actively growing culture of microorganisms of the genus Prototheca in an amount sufficient to produce, after a reasonable growth period, a high cell density. Typical inoculation cell densities are within the range of from about 0.1 g/L to about 15 g/L, preferably from about 0.5 g/L to about 10 g/L and more preferably from about 1 g/L to about 5 g/L, based on the dry weight of the cells. The cells are then grown to a cell density in the range of from about 10 g/L to about 100 g/L preferably from about 20 g/L to about 80 g/L, and more preferably from about 50 g/L to about 70 g/L. The residence times for the microorganisms to reach the desired cell densities during fermentation are typically less than about 200 hours, preferably less than about 120 hours, and more preferably less than about 96 hours.

In one mode of operation of the present invention, the carbon source concentration, such as the glucose concentration, of the fermentation medium is monitored during fermentation. Glucose concentration of the fermentation medium can be monitored using known techniques, such as, for example, use of the glucose oxidase enzyme test or high pressure liquid chromatography, which can be used to monitor glucose concentration in the supernatant, e.g., a cell-free component of the fermentation medium. As stated previously, the carbon source concentration should be kept below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose is used as a carbon source the glucose concentration in the fermentation medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a substantially pure glucose solution, it is preferred to maintain the carbon source concentration of the fermentation medium by addition of aliquots of the original fermentation medium. The use of aliquots of the original fermentation medium are desirable because the concentrations of other nutrients in the medium (e.g. the nitrogen and phosphate sources) can be maintained simultaneously. Likewise, the trace metals concentrations can be maintained in the fermentation medium by addition of aliquots of the trace metals solution.

A further novel aspect of the present invention is a fermentation culture which L-ascorbic acid-producing microalgae and a fermentation medium, wherein the fermentation medium comprises at least about 1 mg/l extracellular L-ascorbic acid and a dissolved oxygen content of at least about 20% saturation. The fermentation culture preferably comprises organisms of the genus Prototheca. Preferably, the pH of said fermentation medium is less than about 6, more preferably less than about 5.5 and most preferably less than about 5.

As stated previously, the present invention provides significant advantages for the production of ascorbic acid. In particular, the organisms of the genus Prototheca as described and used herein produce significant quantities of extracellular L-ascorbic acid. Extracellular L-ascorbic acid can be recovered from the fermentation medium using conventional separation and purification techniques. For example, the fermentation medium can be filtered or centrifuged to remove microorganisms, cell debris and other particulate matter, and L-ascorbic acid can be recovered from the cell-free supernate by conventional methods, such as, for example, ion exchange, chromatography, extraction, solvent extraction, membrane separation, electrodialysis, reverse osmosis, distillation, chemical derivatization and crystallization.

One such example of L-ascorbic acid recovery is provided in U.S. Pat. No. 4,595,659 by Cayle, incorporated herein in its entirety be reference, which discloses the isolation of L-ascorbic acid from an aqueous fermentation medium by ion exchange resin adsorption and elution, which is followed by decoloration, evaporation and crystallization. Further, isolation of the structurally similar isoascorbic acid from fermentation medium by a continuous multi-bed extraction system of anion-exchange resins is described by K. Shimizu, *Agr. Biol. Chem.* 31:346–353 (1967), which is incorporated herein in its entirety by reference.

Intracellular L-ascorbic acid produced in accordance with the present invention can also be recovered and used in a variety of applications. For example, Prototheca cells can be lysed and the ascorbic acid which is released can be recovered by a variety of known techniques. Alternatively, intracellular ascorbic acid can be recovered by washing the cells to extract the ascorbic acid, such as through diafiltration.

In a further aspect of the present invention, intracellular ascorbic acid is recovered by combining microorganisms of the genus Prototheca with food material to enhance the ascorbic acid content of such food material. As used herein, the phrase "food product" refers to any food type fed to humans or non-human animals, including human food and animal feed, with animal feed being preferred. Such animal feed includes, but is not limited to, feed for poultry, swine, horses, cattle and fish. Preferred animal feed can include meat meal, fish meal, corn, corn gluten meal, soybean meal, silage, brewer's grains, hay, alfalfa hay, alfalfa meal, oats, barley, wheat, wheat bran, sorghum, canola meal, rice bran polishings, whole cottonseed and cottonseed meal.

In the embodiment of a food product being an animal food product, the amount of microorganisms typically added to the food product is within the range of from about 0.1% by weight (wt %) and about 5 wt %, more preferably within the range of from about 0.2 wt % and about 2 wt %, and most preferably within the range of from about 0.5 wt % and about 1 wt %. Such food products typically have an ascorbic acid content within the range of from about 0.001 wt % and about 0.25 wt %, more preferably within the range of from about 0.005 wt % and about 0.15 wt %, and most preferably within the range of from about 0.01 wt % and about 0.05 wt %.

The following experimental results are provided for the purposes of illustration and are not intended to limit the scope of the invention. References to "UTEX" strains in the following Examples refer to Prototheca strains obtained from the Culture Collection of Algae, Department of Botany, University of Texas at Austin, Austin, Tex., 78713–7640.

EXAMPLES

Example 1

The following example illustrates the production of L-ascorbic acid by microorganisms of the genus Prototheca, namely, *Prototheca zopfii*. Four fermentations were carried out under the following conditions.

Fermentation Medium Preparation

Trace Metals Solution

The compounds listed in Table 2 and 20 mL of concentrated hydrochloric acid were made up to 1 L with distilled water.

TABLE 2

TRACE METALS SOLUTION

| COMPOUND | CONCENTRATION OF METAL (mg/L) |
|---|---|
| Calcium chloride, dihydrate | 3102 |
| Manganese (II) sulfate, monohydrate | |
| Copper (II) sulfate, monohydrate | 16 |
| Cobalt (II) chloride, pentahydrate | 40 |
| Boric acid | 160 |
| Zinc (II) sulfate, heptahydrate | 400 |
| Sodium molybdate, dihydrate | 19 |
| Vanadyl sulfate, dihydrate | 20 |
| Nickel (II) nitrate, hexahydrate | 8 |
| Sodium selenite | 16 |

Glucose-Salts Medium

The various compounds listed in Table 3 were heat sterilized and combined in a flask after cooling to a final volume of 600 mL.

TABLE 3

Glucose-Salts Medium

| Amount | Compound |
|---|---|
| 56g | Glucose, food grade monohydrate (anhydrous basis) in 80 mL water |
| 0.7g | Trisodium citrate dihydrate |
| 0.46g | Magnesium sulfate, anhydrous |
| 0.7mL | Sulfuric acid in 10 mL water |
| 0.65g | Monobasic sodium phosphate |
| 1.3g | Monobasic potassium phosphate |
| 0.68g | Dibasic sodium phosphate in 10 mL water |
| 9.4mL | Trace Metals Solution (shown above in Table 2) |

Phosphate Medium

A solution containing 0.27 g monobasic potassium phosphate and 0.23 g dibasic sodium phosphate dissolved in 600 mL distilled water was heat-sterilized in a 1 L glass fermentor. After the medium had cooled, 5 mL of a 1.9 g/L ferrous sulfate heptahydrate solution was added through a sterile filter having a pore size of 0.2 $\mu$m.

A 20 mL sample of the Glucose-Salts Medium was added to the Phosphate Medium in the fermentor to form a fermentation medium. The glass fermentor was equipped with an apparatus for agitating the medium and an apparatus for adding oxygen and nutrient components during fermentation.

Cell Growth and L-Ascorbic Acid Production

The fermentation medium was heated and the temperature was maintained at 35° C. Agitation of the fermentation medium began at 300 rpm. Air was sparged into the medium at 0.1 L/min, and the pH of the medium was adjusted to 6.9 with ammonia which was added to the airflow. The fermentation medium was inoculated with an actively growing culture of *Prototheca zopfii*, UTEX 1438, to give an initial cell density of approximately 0.3 g/L by dry weight of the cells.

The cells were grown in the fermentor for the four fermentations to cell densities in the range of from about 20 g/L to about 50 g/L by dry weight of the cells. The pH of the fermentation medium was controlled within the range of from about pH 6.5 to about pH 7 by the addition of gaseous ammonia into the airflow. To maintain an excess of dissolved oxygen in the range of from about 20% to about 90% of the saturation value during the course of the fermentation, agitation of the fermentation medium was gradually increased to 800 rpm. The fermentation medium was aerated by sparging air at a rate of 0.2 L/min into the fermentation medium and was gradually increased during fermentation to 0.6 L/min.

Glucose concentration in the fermentation medium was monitored either by the glucose oxidase enzyme test or by high pressure liquid chromatography by taking a cell-free (supernate) sample of the fermentation medium. When the glucose concentration of the fermentation medium dropped below the original concentration level, it was replenished by adding 20% aliquots of the previously prepared Glucose-Salts Medium to the fermentor, while keeping the total glucose concentration of the fermentation medium below 30 g/L. After the entire prepared amount of Glucose-Salts Medium had been added, the fermentation medium was assayed for L-ascorbic acid.

L-Ascorbic Acid Assay

The method used for quantifying L-ascorbic acid is described by Grun and Loewus, *Analytical Biochemistry*, 130:191–198, (1983). The method is an ion-exchange procedure, using a 7.8×300 mm organic acid analysis column, HPX-87, obtained from Bio-Rad Laboratories in Richmond, Calif. The assay conditions were: mobile phase, 0.013M nitric acid; flow rate 0.8 mL/min; pressure 1500 psig; detection, absorbance at 245 nm. The total L-ascorbic acid (Total L-AA) in the fermentation medium was determined by assaying for ascorbic acid in the fermentation supernate and for ascorbic acid extracted from the cells by contacting cells with 2.5% trichloroacetic acid (TCA) for about 10 minutes.

Cell Density Determinations

For dry weight determinations of cell density, 5 mL whole medium samples were removed from the fermentor and centrifuged at 4000×g for 5 minutes, and the pellet obtained was washed once with distilled water, and then washed into a tared aluminum weighing dish. Cells were dried for a period of time in the range of from about 8 hours to about 24 hours at 60° C., and for an additional hour at 105° C. The dry weight of the cells was calculated by difference. Results expressed as an average of the four fermentations are given below in Table 4.

TABLE 4

| Alga | Temp (° C.) | Dry Cell Weight (g/L) | Total L-AA (mg/L) | mg of L-AA/g of cells (dry weight) |
|---|---|---|---|---|
| Prototheca zopfii UTEX 1438 | 35 | 27.4 | 37.8 | 1.4 |

Example 2

This example illustrates production of extracellular L-ascorbic acid by organisms of the genus Prototheca, namely, *Prototheca zopfii*, at low pH (3.5 to 5). Except as indicated, the procedure of Example 1 was followed.

The fermentation was run in a 14 L fermentor, configured and controlled in the same manner as the 1 L fermentor described in Example 1.

Fermentation Medium Preparation

Glucose-Salts Medium

The Glucose-Salts Medium used is given below in Table 5.

TABLE 5

| Glucose-Salts Medium | |
|---|---|
| Amount | Compound/Component |
| 800g | Glucose, food grade monohydrate (anhydrous basis) in 2.1 L of water |
| 15g | Trisodium citrate dihydrate |
| 6.6g | Magnesium sulfate, anhydrous |
| 10mL | Sulfuric acid in 250 mL water |
| 22g | Monobasic sodium phosphate |
| 22g | Dibasic sodium phosphate in 250 mL water |
| 134mL | Trace Metals Solution (see Table 2 above) |

Phosphate Medium

A solution of 3.9 g monobasic potassium phosphate and 3.3 g dibasic sodium phosphate dissolved in 7.2 L distilled water was heat-sterilized in a 14 L glass fermentor. After the medium had cooled, 27 mL of a 6.0 g/L ferrous sulfate heptahydrate solution was added through a sterile filter having a pore size of 0.2 μm.

Cell Growth and L-Ascorbic Acid Production

The Glucose-Salts Medium listed in Table 5 was added to the Phosphate Medium in the fermentor. In addition, the medium contained 2 mg/L thiamine hydrochloride which was aseptically added to the fermentor after the fermentor had been heat-sterilized and cooled. The temperature of the fermentation medium was brought to and maintained at 30° C. The fermentation medium was inoculated with an actively growing culture of *Prototheca zopfii* strain BTR 1254, to give an initial cell density in the fermentor of about 0.3 g/L by dry weight of the cells.

The cells were grown at a growth rate of 0.20 h$^{-1}$ to a cell density of 56 g/L by dry weight of the cells. The pH was maintained within the range of from about pH 3.5 to about pH 5 by the addition of gaseous ammonia to the fermentation medium. To maintain the dissolved oxygen content of the fermentation medium within the range of from about 20% to about 90% of its saturation point, agitation of the fermentation medium began at 100 rpm and was gradually increased during fermentation to 800 rpm. Likewise, the fermentation medium was aerated by sparging air into the fermentation medium at a rate of 2.0 L/min and was gradually increased during fermentation to 6.0 L/min. Conditions and analytical results are summarized below in Table 6.

TABLE 6

| Time (hr) | pH | Dry Cell Weight (g/L) | Total L-AA (mg/L) | Supernatant L-AA (mg/L) | Comments |
|---|---|---|---|---|---|
| 6 | 5.0 | 0.6 | | | |
| 12 | 4.8 | 3.3 | | | 250 rpm; 200 mL[a] |
| 21 | | | | | 350 rpm; 4.0 L/min |
| 22 | 5.0 | 15.9 | | | 400 mL |
| 24 | 3.8 | 24.0 | 34.6 | 11.2 | 6.0 L/min; 500 mL |
| 25 | 4.0 | 32.2 | 39.7 | 15.8 | 800 rpm[b] |
| 27 | 3.9 | 48.6 | 58.6 | 27.0 | |
| 28 | 4.0 | 53.6 | 71.6 | 71.6 | dissolved oxygen measured zero |
| 29 | 4.0 | 55.8 | 73.5 | 73.5 | |

[a]Glucose-Salts Medium.
[b]1050 mL of Glucose-Salts Medium added over the next 3 hr.

As shown in Table 6 above, the concentrations of extracellular and intracellular L-ascorbic acid near the end of the fermentation run are identical. In addition, a significant amount of extracellular L-ascorbic acid was measured in the fermentation medium, even with measurable dissolved oxygen in the fermentation medium.

Example 3

This example illustrates production of L-ascorbic acid by organisms of the genus Prototheca, namely, *Prototheca moriformis* at low pH (4 to 5). Except where indicated, the procedure of Example 2 was followed.

Cell Growth and L-Ascorbic Acid Production

In addition to the ingredients listed in Table 3, the fermentation medium contained 2 mg/L thiamine hydrochloride, which was aseptically added to the fermentor after the fermentor had been heat-sterilized and cooled. The temperature of the fermentation medium was brought to and maintained at 30° C.

The fermentation medium was inoculated with an actively growing culture of *Prototheca moriformis*, ATCC 75669 to give an initial cell density in the fermentation medium of about 0.3 g/L by dry weight of the cells. The cells were grown at a growth rate of 0.23 h$^{-1}$ to obtain a cell density of 42 g/L by dry weight of the cells. For the first 22 hours, the pH of the fermentation medium was maintained at about pH 5 by the addition of gaseous anhydrous ammonia to the fermentation medium. After this time, the addition of ammonia to the fermentation medium was stopped. When the pH was measured to have dropped to pH 4, the addition of ammonia to the fermentation medium was resumed, and the pH of the fermentation medium was maintained at pH 4 for the remainder of the fermentation. Results for the fermentation are summarized in Table 7.

As shown in Table 7, the concentrations of extracellular and intracellular L-ascorbic acid produced are identical. In addition, a significant amount of extracellular L-ascorbic acid was measured in the fermentation medium, even with measurable dissolved oxygen in the fermentation medium.

TABLE 7

| Time (hr) | pH | Dry Cell Weight (g/L) | Total L-AA (mg/L) | Supernate L-AA (mg/L) | mg of L-AA/g of Cells (dry weight) | Comments |
|---|---|---|---|---|---|---|
| 11 | 5.0 | 0.9 | | | | |
| 12 | | | | | | 250 rpm |
| 17 | 4.8 | 3.9 | | | | 400 rpm; 3.0 L/min; 200 mL[a] |
| 20 | 5.2 | 8.2 | | | | 400 rpm |
| 21 | | | | | | 500 mL; 4 L/min |
| 22 | 5.2 | 10.8 | | | | 400 mL[b] |
| 24 | | | | | | 800 rpm; 5 L/min |
| 26 | 4.3 | 27.7 | 105 | 109 | 3.8 | |
| 28 | 4.1 | 34.5 | 132 | 140 | 3.8 | 850 rpm |
| 30 | 4.1 | 41.9 | 150 | 162 | 3.8 | |

[a]Glucose-Salts Medium.
[b]1115 mL of Glucose-Salts Medium added over the next 6 hr.

Example 4

The following example illustrates ascorbic acid production by five known species of Prototheca: *P. moriformis, P. zopfii, P. wickerhamii, P. stagnora* and *P. ulmea*.

Fermentation Medium Preparation

The fermentation medium used for the strains contained potassium phosphate monobasic 0.82 g/L, potassium phosphate dibasic 4.2 g/L, trisodium citrate 7.7 g/L, magnesium sulfate 0.6 g/L, ammonium sulfate 3.5 g/L, trace metals solution (as shown in Table 2 above) of 2 mL/L, yeast extract 2.5 g/L, glucose 30 g/L, and thiamine HCl 1 mg/L. The growth medium had a starting pH of about 7.

Cell Growth and L-Ascorbic Acid Production

A total of forty-three wild type strains of these five different species were cultured under the following conditions. Cells of each strain were inoculated into 50 mL of the previously prepared fermentation medium in 250 mL baffled Erlenmeyer flasks and incubated at 30° C. while being agitated at 160 rpm.

When optical density readings indicated that cell density was high enough for accurate ascorbic acid assay, whole medium samples were withdrawn for analysis. For the ascorbic acid assay, 2.0 mL samples of whole medium were combined with 250 μL of 25% trichloroacetic acid, mixed, and allowed to stand 15 minutes to extract. This whole medium extract was centrifuged to pellet the cells and the supernate was assayed for ascorbic acid. The ascorbic acid standards were prepared from 10,000 mg/L ascorbic acid stock solution in 5% trichloroacetic acid. The reaction mixture was prepared by 250 μL of whole medium extract (or ascorbic acid standard for baseline), 100 μL of o-phosphoric acid, and 2 mL of color reagent. The color reagent used was prepared by combining four parts of 0.5% 2, 2'-dipyridyl with one part 8.3 mM ferric ammonium sulfate. The mixture was allowed to stand one hour at room temperature, and its absorbance was read at 525 nm. Ascorbic acid concentrations were calculated based on observances of the ascorbic acid standards.

For dry weight determinations, 5 mL of each culture was centrifuged to pellet cells, the supernates were decanted, and cells were resuspended in 5 mL of distilled water and recentrifuged. Supernates were again decanted, and the washed cells were washed into tared aluminum weighing dishes. Cells were dried at 60° C. overnight and 105° C. for an additional two hours. Pans with dried cells were cooled in a desiccator and weighed. Cell dry weights were calculated by difference.

The results of these experiments, as shown in Table 8, clearly indicate that all forty-three wild type strains tested of the known five species of Prototheca produced ascorbic acid.

TABLE 8

ASCORBIC ACID PRODUCTION BY PROTOTHECA STRAINS

| Prototheca Species | Strain No. | L-Ascorbic Acid (mg) per gram of dry cell weight | Growth rate, h − 1 |
|---|---|---|---|
| P. zopfii | BTR 1263 | 2.40 | 1.178 |
| P. zopfii | BTR 1213 | 1.50 | 0.254 |
| P. moriformis | BTR 1385 | 1.80 | 0.186 |
| P. zopfii | BTR 879 | 1.70 | 0.194 |
| P. zopfii | BTR 1254 | 1.10 | 0.216 |
| P. stagnora | UTEX 1443 | 4.80 | 0.043 |
| P. zopfii | BTR 1403 | 1.30 | 0.123 |
| P. wickerhamii | BTR 972 | 0.74 | 0.176 |
| P. moriformis | UTEX 1439 | 0.69 | 0.175 |
| P. ulmea | BTR 1277 | 0.63 | 0.112 |
| P. ulmea | BTR 1275 | 1.20 | 0.049 |
| P. moriformis | BTR 1080 | 1.70 | 0.027 |
| P. zopfii | BTR 1407 | 4.80 | 0.145 |
| P. zopfii | BTR 1205 | 2.00 | 0.332 |
| P. zopfii | BTR 883 | 4.00 | 0.126 |
| P. zopfii | BTR 1218 | 2.40 | 0.174 |
| P. zopfii | BTR 1177 | 2.20 | 0.172 |
| P. zopfii | BTR 946 | 2.10 | 0.167 |
| P. chlorelloides* | UTEX 178 | 2.40 | 0.145 |
| P. moriformis | UTEX 1434 | 2.10 | 0.162 |
| P. zopfii | BTR 871 | 1.80 | 0.184 |
| P. zopfii | BTR 1183 | 1.70 | 0.192 |
| P. zopfii | BTR 1078 | 1.90 | 0.169 |
| P. kruegeri* | UTEX 329 | 2.25 | 0.140 |
| P. zopfii | BTR 1043 | 1.80 | 0.172 |
| P. zopfii | BTR 1145 | 1.60 | 0.188 |
| P. zopfii | UTEX 1438 | 1.60 | 0.176 |
| P. zopfii | BTR 1034 | 1.40 | 0.193 |
| P. moriformis | BTR 1181 | 1.70 | 0.151 |
| P. zopfii | BTR 1140 | 1.60 | 0.157 |
| P. moriformis | UTEX 288 | 1.40 | 0.172 |
| P. zopfii | BTR 899 | 3.00 | 0.080 |
| P. zopfii | BTR 1368 | 2.10 | 0.109 |
| P. zopfii | BTR 1110 | 1.10 | 0.179 |
| P. zopfii | BTR 893 | 1.20 | 0.153 |
| P. zopfii | BTR 948 | 1.20 | 0.146 |
| P. zopfii | BTR 1367 | 0.82 | 0.206 |
| P. zopfii | BTR 1369 | 0.87 | 0.187 |
| P. zopfii | BTR 1002 | .98 | 0.163 |
| P. zopfii | BTR 870 | 0.82 | 0.190 |
| P. zopfii | BTR 1250 | 0.92 | 0.164 |
| P. zopfii | ATCC 16527 | 0.94 | 0.146 |
| P. zopfii | BTR 1334 | 0.73 | 0.141 |

*These strains were named prior to the reclassification of Prototheca into five separate species.

*Prototheca zopfii* BTR 883, was deposited as ATCC No. 209695, on Mar. 25, 1998, with the American Type Culture Collection (ATCC), 10801 University Boulevard, Manassas, Va. 20110, USA, under the terms of the Budapest Treaty on the International Recognition of the Deposit of Microorganisms for the Purpose of Patent Procedure.

*Prototheca zopfii* BTR 1407, was deposited as ATCC No. 209696, on Mar. 25, 1998, with the American Type Culture Collection (ATCC), 10801 University Boulevard, Manassas, Va. 20110, USA, under the terms of the Budapest Treaty on the International Recognition of the Deposit of Microorganisms for the Purpose of Patent Procedure.

Example 5

The following example further illustrates the production of L-ascorbic acid by organisms of the genus Prototheca, namely, *Prototheca moriformis* at a variety of fermentation temperatures.

Cell Growth

Cells of *P. moriformis* were inoculated from agar slants into 250 mL baffled Ehrlenmeyer flasks containing 50 mL of inoculum medium at a pH of 7.2, comprised of 0.82 g/L monobasic potassium phosphate, 4.2 g/L dibasic potassium phosphate, 7.7 g/L trisodium citrate, 0.2 g/L magnesium sulfate, 3.5 g/L ammonium sulfate, 2 mL/L of the trace metals solution described previously in Table 1, 20 g/L glucose and 1 mg/L of thiamine HCl, and incubated at 35° C. using a stirring rate of 200 rpm for 24 hours.

Flasks containing a second medium identical to the inoculum medium, except that the glucose concentration was 30 g/L, were inoculated from the inoculum flasks to an $A_{620}$ of 0.15, and incubated at a stirring rate of 200 rpm at constant temperature for a variety of temperatures. Whole broth samples were withdrawn for analysis and data was obtained for the fermentation medium at either 24 or 48 hours after inoculation.

from 25,000 mg/L ascorbic acid stock solution in 5 mM phosphate/20 mM citrate buffer, having a pH of 4.5. The reaction mixture was prepared in wells of a 96-well microliter plate by adding 25 μL of medium supernate (or ascorbic acid standard for baseline), and 125 μL of color reagent. The color reagent used was prepared by combining four parts of 0.5% 2, 2'-dipyridyl with one part 8.3 mM ferric ammonium sulfate in 21.6% o-phosphoric acid. The mixture was allowed to stand one hour at room temperature, and its absorbance was read at 525 nm. Ascorbic acid concentrations were calculated based on observances of the ascorbic acid standards.

The results for three fermentations at various temperatures are shown in Table 9.

As seen in Table 9, organisms of the genus Prototheca, namely *P. moriformis* are capable of producing ascorbic acid at fermentation temperatures between 25° C. and 35° C.

TABLE 9

*Prototheca moriformis* ATCC 75669
Cultured at Different Temperatures

| Carbon Source | Nitrogen Source | Temp C. | Starting pH | Ending pH | Cell Dry Weight g/L | Ascorbic Acid, mg/L | Specific Formation mg AA/g Cells (dry weight) |
|---|---|---|---|---|---|---|---|
| Glucose | Ammonium | 25 | 7.2 | 4.8 | 10.6 | 41.4 | 3.9 |
| Glucose | Ammonium | 30 | 7.2 | 5.0 | 12.6 | 51.9 | 4.1 |
| Glucose | Ammonium | 35 | 7.2 | 4.7 | 11.3 | 40.0 | 3.5 |

Cell Dry Weight Determinations

For cell dry weight determinations, 2.5 mL samples of each culture were centrifuged to pellet the cells, the supernates were decanted, and cells were resuspended in 5 mL of distilled water and recentrifuged. Supernates were again decanted and the cells were washed into tared aluminum weighing dishes. Cells were dried at 60° C. overnight, and at 150° C. for an additional two hours. Pans with dried cells were cooled in a desiccator and weighed. Cell dry weights were calculated by difference.

Ascorbic Acid Assay

The supernates were assayed for ascorbic acid by the following process. Ascorbic acid standards were prepared

Example 6

The following example further illustrates the production of L-ascorbic acid by organisms of the genus Prototheca, namely, *Prototheca moriformis* at a variety of fermentation medium pHs.

Except for the pH of the fermentation medium for each trial, the procedure of Example 5 was followed. The results for three fermentations at various fermentation medium pH are shown in Table 10.

As seen in Table 10, organisms of the genus Prototheca, namely *P. moriformis* are capable of producing ascorbic acid at fermentation pH from 7.2 to 3.3.

TABLE 10

*Prototheca moriformis* ATCC 75669
Cultured at Different pH

| Carbon Source | Nitrogen Source | Temp C. | Starting pH | Ending pH | Dry Weight g/L | Ascorbic Acid, mg/L | Specific Formation mg AA/g cells |
|---|---|---|---|---|---|---|---|
| Glucose | Ammonium | 35 | 7.2 | 4.7 | 11.3 | 40.0 | 3.5 |
| Glucose | Ammonium | 35 | 5.8 | 5.3 | 10.6 | 36.7 | 3.5 |
| Glucose | Ammonium | 35 | 4.5 | 3.3 | 13.2 | 41.6 | 3.2 |

Example 7

The following example further illustrates the production of L-ascorbic acid by organisms of the genus Prototheca, namely, *Prototheca moriformis* using a variety of nitrogen sources in the fermentation medium.

Except for the varied nitrogen sources, the procedure of Example 5 was followed. When urea was used as the nitrogen source, it was added to the second medium at 1.6 g/L, when casamino acid was used as the nitrogen source, it was added to the second medium at 6.6 g/L, and when monosodium glutamate was used as the nitrogen source, it was added to the second medium at 6.6 g/L. The results for four fermentations using various nitrogen sources are shown in Table 11.

As seen in Table 11, organisms of the genus Prototheca, namely *P. moriformis* are capable of producing ascorbic acid using various nitrogen sources.

TABLE 11

*Prototheca moriformis* ATCC 75669
Cultured Using Different Nitrogen Sources

| Carbon Source | Nitrogen Source | Temp C. | Starting pH | Ending pH | Dry Weight g/L | Ascorbic Acid, mg/L | Specific Formation mg AA/g cells |
|---|---|---|---|---|---|---|---|
| Glucose | Ammonium | 35 | 7.2 | 4.7 | 11.3 | 40.0 | 3.5 |
| Glucose | Urea | 35 | 7.2 | 7.2 | 1.4 | 1.9 | 1.4 |
| Glucose | Glutamate | 35 | 7.2 | 4.8 | 11.3 | 61.2 | 5.4 |
| Glucose | Casamino Acids | 35 | 7.2 | 6.6 | 11.5 | 47.3 | 4.1 |

Example 8

The following example further illustrates the production of L-ascorbic acid by organisms of the genus Prototheca, namely, *Prototheca moriformis* using a variety of carbon sources in the fermentation medium.

Except for the varied carbon sources, the procedure of Example 5 was followed. When ethanol was used as the carbon source, it was added to the second medium at 23 g/L, when n-propanol was used as the nitrogen source, it was added to the second medium at 20 g/L, when glycerol was used as the nitrogen source, it was added to the second medium at 29 g/L, and when fructose was used as the nitrogen source, it was added to the second medium at 30 g/L. The results for five fermentations using various carbon sources are shown in Table 12.

As seen in Table 12, organisms of the genus Prototheca, namely *P. moriformis* are capable of producing ascorbic acid using various carbon sources.

Example 9

The following example further illustrates the production of L-ascorbic acid by organisms of the genus Prototheca, namely, *Prototheca wickerhamii* at a variety of fermentation temperatures.

The procedure of Example 5 was followed. The results for three fermentations at various temperatures are shown in Table 13.

As seen in Table 13, organisms of the genus Prototheca, namely *P. wickerhamii* are capable of producing ascorbic acid at fermentation temperatures between 25° C. and 35° C.

TABLE 12

*Prototheca moriformis* ATCC 75669
Cultured Using Different Glucose Sources

| Carbon Source | Nitrogen Source | Temp C. | Starting pH | Ending pH | Dry Weight g/L | Ascorbic Acid, mg/L | Specific Formation mg AA/g cells |
|---|---|---|---|---|---|---|---|
| Glucose | Ammonium | 35 | 7.2 | 4.7 | 11.3 | 40.0 | 3.5 |
| Ethanol | Ammonium | 35 | 7.2 | 5.3 | 8.4 | 37.9 | 4.5 |
| n-propanol | Ammonium | 35 | 7.2 | 4.6 | 2.0 | 6.7 | 3.4 |
| glycerol | Ammonium | 35 | 7.2 | 5.3 | 7.7 | 30.8 | 4.0 |
| fructose | Ammonium | 35 | 7.2 | 5.3 | 9.4 | 43.2 | 4.6 |

TABLE 13

*Prototheca wickerhamii* ATCC 16529
Cultured at Different Temperatures

| Carbon Source | Nitrogen Source | Temp C. | Starting pH | Ending pH | Dry Weight g/L | Ascorbic Acid, mg/L | Specific Formation mg AA/g cells |
|---|---|---|---|---|---|---|---|
| Glucose | Ammonium | 25 | 7.2 | 4.8 | 11.9 | 4.2 | 0.4 |
| Glucose | Ammonium | 30 | 7.2 | 4.6 | 9.8 | 3.3 | 0.3 |
| Glucose | Ammonium | 35 | 7.2 | 4.8 | 12.2 | 2.4 | 0.2 |

Example 10

The following example further illustrates the production of L-ascorbic acid by organisms of the genus Prototheca, namely, *Prototheca wickerhamii* at a variety of fermentation medium pHs.

Except for the pH of the fermentation medium for each trial, the procedure of Example 5 was followed. The results for three fermentations at various fermentation medium pH are shown in Table 14.

As seen in Table 14, organisms of the genus Prototheca, namely *P. wickerhamii* are capable of producing ascorbic acid at fermentation pH from 7.2 to 2.7.

Except for the varied nitrogen sources, the procedure of Example 5 was followed. When urea was used as the nitrogen source, it was added to the second medium at 1.6 g/L, when casamino acid was used as the nitrogen source, it was added to the second medium at 6.6 g/L, and when monosodium glutamate was used as the nitrogen source, it was added to the second medium at 6.6 g/L. The results for four fermentations using various nitrogen sources are shown in Table 15.

As seen in Table 15, organisms of the genus Prototheca, namely *P. wickerhamii* are capable of producing ascorbic acid using various nitrogen sources.

TABLE 14

*Prototheca wickerhamii* ATCC 16529
Cultured at Different pH

| Carbon Source | Nitrogen Source | Temp C. | Starting pH | Ending pH | Dry Weight g/L | Ascorbic Acid, mg/L | Specific Formation mg AA/g cells |
|---|---|---|---|---|---|---|---|
| Glucose | Ammonium | 35 | 7.2 | 4.8 | 12.2 | 2.4 | 0.2 |
| Glucose | Ammonium | 35 | 5.8 | 3.5 | 10.6 | 2.9 | 0.3 |
| Glucose | Ammonium | 35 | 4.5 | 2.7 | 6.7 | 9.5 | 1.4 |

TABLE 15

*Prototheca wickerhamii* ATCC 16529
Cultured Using Different Nitrogen Sources

| Carbon Source | Nitrogen Source | Temp C. | Starting pH | Ending pH | Dry Weight g/L | Ascorbic Acid, mg/L | Specific Formation mg AA/g cells |
|---|---|---|---|---|---|---|---|
| Glucose | Ammonium | 35 | 7.2 | 4.8 | 12.2 | 2.4 | 0.2 |
| Glucose | Urea | 35 | 7.2 | 7.2 | 7.7 | 2.6 | 0.3 |
| Glucose | Glutamate | 35 | 7.2 | 4.6 | 3.2 | 2.8 | 0.9 |
| Glucose | Casamino Acids | 35 | 7.2 | 5.8 | 11.0 | 5.7 | 0.5 |

Example 11

The following example further illustrates the production of L-ascorbic acid by organisms of the genus Prototheca, namely, *Prototheca wickerhamii* using a variety of nitrogen sources in the fermentation medium.

Example 12

The following example further illustrates the production of L-ascorbic acid by organisms of the genus Prototheca, namely, *Prototheca wickerhamii* using a variety of carbon sources in the fermentation medium.

Except for the varied carbon sources, the procedure of Example 5 was followed. When ethanol was used as the carbon source, it was added to the second medium at 23 g/L, when n-propanol was used as the nitrogen source, it was added to the second medium at 20 g/L, when glycerol was used as the nitrogen source, it was added to the second medium at 29 g/L, and when fructose was used as the nitrogen source, it was added to the second medium at 30 g/L. The results for five fermentations using various carbon sources are shown in Table 16.

As seen in Table 16, organisms of the genus Prototheca, namely *P. wickerhamii* are capable of producing ascorbic acid using various carbon sources.

Example 14

The following example further illustrates the production of L-ascorbic acid by organisms of the genus Prototheca, namely, *Prototheca zopfii* at a variety of fermentation medium pHs.

Except for the pH of the fermentation medium for each trial, the procedure of Example 5 was followed. The results for three fermentations at various fermentation medium pH are shown in Table 18.

As seen in Table 18, organisms of the genus Prototheca, namely *P. zopfii* are capable of producing ascorbic acid at fermentation pH from 7.2 to 2.7.

TABLE 16

*Prototheca wickerhamii* ATCC 16529
Cultured Using Different Carbon Sources

| Carbon Source | Nitrogen Source | Temp C. | Starting pH | Ending pH | Dry Weight g/L | Ascorbic Acid, mg/L | Specific Formation mg AA/g cells |
|---|---|---|---|---|---|---|---|
| Glucose | Ammonium | 35 | 7.2 | 4.8 | 12.2 | 2.4 | 0.2 |
| Ethanol | Ammonium | 35 | 7.2 | 4.9 | 8.2 | 1.0 | 0.1 |
| n-propanol | Ammonium | 35 | 7.2 | 6.6 | 0.3 | 1.1 | 3.9 |
| glycerol | Ammonium | 35 | 7.2 | 5.3 | 7.1 | 1.1 | 0.2 |
| fructose | Ammonium | 35 | 7.2 | 4.9 | 11.8 | 1.6 | 0.1 |

Example 13

The following example further illustrates the production of L-ascorbic acid by organisms of the genus Prototheca, namely, *Prototheca zopfii* at a variety of fermentation temperatures.

The procedure of Example 5 was followed. The results for three fermentations at various temperatures are shown in Table 17.

As seen in Table 17, organisms of the genus Prototheca, namely *P. zopfii* are capable of producing ascorbic acid at fermentation temperatures between 25° C. and 35° C.

TABLE 17

*Prototheca zopfii* BTR 946
Cultured at Different Temperatures

| Carbon Source | Nitrogen Source | Temp C. | Starting pH | Ending pH | Dry Weight g/L | Ascorbic Acid, mg/L | Specific Formation mg AA/g cells |
|---|---|---|---|---|---|---|---|
| Glucose | Ammonium | 25 | 7.2 | 4.7 | 3.2 | 13.7 | 4.3 |
| Glucose | Ammonium | 30 | 7.2 | 4.8 | 5.7 | 16.1 | 2.8 |
| Glucose | Ammonium | 35 | 7.2 | 4.8 | 4.0 | 17.1 | 4.3 |

TABLE 18

*Prototheca zopfii* BTR 946
Cultured at Different pH

| Carbon Source | Nitrogen Source | Temp C. | Starting pH | Ending pH | Dry Weight g/L | Ascorbic Acid, mg/L | Specific Formation mg AA/g cells |
|---|---|---|---|---|---|---|---|
| Glucose | Ammonium | 35 | 7.2 | 4.8 | 4.0 | 17.1 | 4.3 |
| Glucose | Ammonium | 35 | 5.8 | 3.9 | 2.8 | 21.5 | 7.7 |
| Glucose | Ammonium | 35 | 4.5 | 2.8 | 10.2 | 40.1 | 3.9 |

Example 15

The following example further illustrates the production of L-ascorbic acid by organisms of the genus Prototheca, namely, *Prototheca zopfii* using a variety of nitrogen sources in the fermentation medium.

Except for the varied nitrogen sources, the procedure of Example 5 was followed. When urea was used as the nitrogen source, it was added to the second medium at 1.6 g/L, when casamino acid was used as the nitrogen source, it was added to the second medium at 6.6 g/L, and when monosodium glutamate was used as the nitrogen source, it was added to the second medium at 6.6 g/L. The results for four fermentations using various nitrogen sources are shown in Table 19.

As seen in Table 19, organisms of the genus Prototheca, namely *P. zopfii* are capable of producing ascorbic acid using various nitrogen sources.

Example 16

The following example further illustrates the production of L-ascorbic acid by organisms of the genus Prototheca, namely, *Prototheca zopfii* using a variety of carbon sources in the fermentation medium.

Except for the varied carbon sources, the procedure of Example 5 was followed. When ethanol was used as the carbon source, it was added to the second medium at 23 g/L, when n-propanol was used as the nitrogen source, it was added to the second medium at 20 g/L, when glycerol was used as the nitrogen source, it was added to the second medium at 29 g/L, and when fructose was used as the nitrogen source, it was added to the second medium at 30 g/L. The results for five fermentations using various carbon sources are shown in Table 20.

As seen in Table 20, organisms of the genus Prototheca, namely *P. zopfii* are capable of producing ascorbic acid using various carbon sources.

TABLE 19

*Prototheca zopfii* BTR 946
Cultured Using Different Nitrogen Sources

| Carbon Source | Nitrogen Source | Temp C. | Starting pH | Ending pH | Dry Weight g/L | Ascorbic Acid, mg/L | Specific Formation mg AA/g cells |
|---|---|---|---|---|---|---|---|
| Glucose | Ammonium | 35 | 7.2 | 4.8 | 4.0 | 17.1 | 4.3 |
| Glucose | Urea | 35 | 7.2 | 7.0 | 1.4 | 2.9 | 2.1 |
| Glucose | Glutamate | 35 | 7.2 | 4.5 | 7.1 | 25.3 | 3.6 |
| Glucose | Casamino Acids | 35 | 7.2 | 6.6 | 10.1 | 27.2 | 2.7 |

TABLE 20

*Prototheca zopfii* BTR 946
Cultured Using Different Carbon Sources

| Carbon Source | Nitrogen Source | Temp C. | Starting pH | Ending pH | Dry Weight g/L | Ascorbic Acid, mg/L | Specific Formation mg AA/g cells |
|---|---|---|---|---|---|---|---|
| Glucose | Ammonium | 35 | 7.2 | 4.8 | 4.0 | 17.1 | 4.3 |
| Ethanol | Ammonium | 35 | 7.2 | 4.8 | 1.9 | 1.9 | 1.0 |
| n-propanol | Ammonium | 35 | 7.2 | 5.3 | 5.5 | 2.4 | 0.4 |
| glycerol | Ammonium | 35 | 7.2 | 4.8 | 7.3 | 5.0 | 0.7 |
| fructose | Ammonium | 35 | 7.2 | 4.8 | 3.5 | 15.2 | 4.3 |

While various embodiments of the present invention have been described in detail, it is apparent that modifications and adaptations of those embodiments will occur to those skilled in the art. However, it is to be expressly understood that such modifications and adaptations are within the scope of the present invention, as set forth in the following claims.

What is claimed is:

1. A process for the production of L-ascorbic acid, the process comprising the steps of:
    (a) culturing an organism of the genus Prototheca in a fermentation medium containing assimilable sources of carbon and nitrogen; and
    (b) recovering L-ascorbic acid produced by said organism during said step of culturing.

2. The process claimed in claim 1, wherein said organism is *Prototheca moriformis*.

3. The process claimed in claim 1, wherein said organism is *Prototheca wickerhamii*.

4. The process claimed in claim 1, wherein said organism is *Prototheca zopfii*.

5. The process claimed in claim 1, wherein said fermentation medium has a pH of less than about 6.

6. The process claimed in claim 1, wherein said fermentation medium has a pH of less than about 5.5.

7. The process claimed in claim 1, wherein said fermentation medium has a pH of less than about 5.

8. The process claimed in claim 1, wherein said organism of the genus Prototheca produces extracellular L-ascorbic acid, and extracellular L-ascorbic acid accumulates in said fermentation medium.

9. The process claimed in claim 1, wherein said step of recovering L-ascorbic acid comprises recovering extracellular L-ascorbic acid produced by said organism from said fermentation medium.

10. The process claimed in claim 9, wherein said step of recovering L-ascorbic comprises a process selected from the group consisting of ion exchange, chromatography, extraction, solvent extraction, electrodialysis, membrane separation, reverse osmosis, distillation, chemical derivatization and crystallization.

11. The process claimed in claim 1, wherein said step of recovering comprises the step of recovering intracellular L-ascorbic acid from said organism.

12. The process claimed in claim 1, wherein at least about 10% of said L-ascorbic acid is extracellular.

13. The process claimed in claim 1, wherein at least about 25% of said L-ascorbic acid is extracellular.

14. The process claimed in claim 1, wherein at least about 50% of said L-ascorbic acid is extracellular.

15. The process claimed in claim 1, wherein the cell density of said organism in said fermentation medium is within the range of from about 10 g/l to about 100 g/L based on the dry weight of the cells.

16. A process for the production of L-ascorbic acid, the process comprising the steps of:
    (a) culturing an organism of the genus Prototheca in a fermentation medium having a pH of less than about 6 and an available source of oxygen until said fermentation medium has a concentration of extracellular L-ascorbic acid of greater than about 1 mg/l; and
    (b) recovering extracellular L-ascorbic acid from said fermentation medium.

17. The process claimed in claim 16, wherein said step of recovering extracellular L-ascorbic acid from said fermentation medium comprises a process selected from the group consisting of ion exchange, chromatography, extraction, solvent extraction, electrodialysis, membrane separation, reverse osmosis, distillation, chemical derivatization and crystallization.

18. The process claimed in claim 16, wherein said organism comprises *Prototheca moriformis*.

19. The process claimed in claim 16, wherein said organism is *Prototheca zopfii*.

20. The process claimed in claim 16, wherein said organism is *Prototheca wickerhamii*.

21. The process claimed in claim 16, wherein said fermentation medium has a pH of less than about 6.

22. The process claimed in claim 16, wherein said fermentation medium has a pH of less than about 5.5.

23. The process claimed in claim 16, wherein said fermentation medium has a pH of less than about 5.

* * * * *